United States Patent [19]
Lennox et al.

[11] Patent Number: 5,545,195
[45] Date of Patent: Aug. 13, 1996

[54] INTERSTITIAL HEATING OF TISSUE

[75] Inventors: Charles D. Lennox, Hudson, N.H.;
Troy W. Roberts, Arlington, Mass.

[73] Assignee: Boston Scientific Corporation,
Watertown, Mass.

[21] Appl. No.: 283,986

[22] Filed: Aug. 1, 1994

[51] Int. Cl.⁶ .................................................. A61F 7/12
[52] U.S. Cl. ............................ 607/105; 607/113; 606/28
[58] Field of Search ........................... 604/113, 114;
606/27, 28, 29, 30, 31; 607/96, 98, 99,
113, 105

[56] References Cited

U.S. PATENT DOCUMENTS

| 4,955,377 | 9/1990 | Lennox et al. ........................ 128/401 |
| 5,006,119 | 4/1991 | Acker et al. ............................. 606/28 |
| 5,103,804 | 4/1992 | Abele et al. ............................. 128/4 |
| 5,122,137 | 6/1992 | Lennox ..................................... 606/40 |
| 5,151,100 | 9/1992 | Abele et al. ............................. 606/28 |
| 5,292,321 | 3/1994 | Lee ........................................... 606/28 |
| 5,336,222 | 8/1994 | Durgin, Jr. et al. ..................... 606/50 |

FOREIGN PATENT DOCUMENTS

| WO92/03095 | 3/1992 | WIPO .............................. A61B 8/12 |
| WO94/07446 | 4/1994 | WIPO .............................. A61F 7/12 |

OTHER PUBLICATIONS

Akamatsu et al., "Development and Evaluation of a Needle for Percutaneous Ethanol Injection Therapy," 1993, Radiology, vol. 186, No. 1, pp. 284–286.

Babbs et al., "Theoretical Basis for Controlling Minimal Tumor Temperature During Interstitial Conductive Heat Therapy" Jul., 1990, IEEE Transactions on Biomedical Engineering, vol. 37, No. 7, pp. 662–672.

Bales et al., "Initial Outcomes with Cryosurgery in Prostate Cancer Patients Having Failed Radiation Therapy," date unknown.

Cohen et al., "Cryosurgical Ablation of the Prostate (CSAP) as Used in the Patient Who Has Failed Radiation Therapy," date unknown.

Cohen et al., "Cryosurgical Ablation of the Prostate(CSAP) in Patients with Clinical Stage A, B and C Adenocarcinoma of the Prostate; Outcomes of PSA and Biopsy at 3, 12 and 24 Months," date unknown.

Daikuzono et al., "Computer Controlled Contact Nd:YAG Laser System for Interstitial Local Hyperthermia and PDT," 1988, SPIE vol. 907 Laser Surgery: Characterization and Therapeutics, pp. 75–79.

Futatsuki et al., "Some Attempts for Improvement of Balloon Laserthermia," 1990, SPIE vol. 1201 Optical Fibers in Medicine V, pp. 625–636.

Hynynen et al., "Hyperthermia in Cancer Treatment," Jul., 1990, Investigative Radiology, vol. 25, pp. 824–834.

(List continued on next page.)

Primary Examiner—Angela D. Sykes
Assistant Examiner—Eric F. Winakur
Attorney, Agent, or Firm—Fish & Richardson P.C.

[57] ABSTRACT

An elongated, rigid implement having a sharp distal end is insertable into a solid mass within the body of a living being through a puncture site in the solid mass created by the sharp distal end. An elongated sleeve, which engages the elongated, rigid implement, is insertable into the solid mass through the puncture site in the solid mass. Fluid is provided to an expandable chamber located in the vicinity of a distal end of the elongated sleeve through at least one channel located within the elongated sleeve, to inflate the chamber while the chamber is positioned interstitially within the solid mass. A heating device located within the expandable chamber is powered, through at least one elongated conductor located within the elongated sleeve, to heat fluid within the chamber while the chamber is filled with the fluid and is positioned interstitially within the solid mass. The inflation of the chamber while the chamber is positioned interstitially within the solid mass causes compressive ischemia of tissue surrounding the chamber, and the compressive ischemia of the tissue surrounding the chamber reduces a heat sink effect of the tissue during powering of the heating device.

20 Claims, 6 Drawing Sheets

OTHER PUBLICATIONS

McKiel, Jr., "PSA and Post Treatment Biopsy Results After Cryosurgery for States $T_1$–$T_3$ Prostate Cancer," date unknown.

Rossi et al., "Percutaneous Ultrasound–Guided Radiofrequency Electrocautery for the Treatment of Small Hepatocellular Carcinoma," 1993, Journal of Interventional Radiology, vol. 8, pp. 97–103.

Wang et al., "Laserthermia for the Treatment of Small Hepatocellular Carcinoma: A Preliminary Study," 1990 SPIE vol. 1201 Optical Fibers in Medicine V, pp. 620–624.

INTERSTITIAL HEATING OF TISSUE

BACKGROUND OF THE INVENTION

This invention relates to interstitial heating of tissue and in particular to heating of a solid mass within a body of a living being by means of an expandable chamber positioned interstitially within the solid mass. As used herein the term "interstitial" means situated between the cellular elements of a structure.

Various methods of interstitial necrosis are known that involve puncturing of a solid organ and insertion of a non-expandable interstitial device into the solid organ. The interstitial device may be used for electro-surgery, cryo-ablation, laser ablation, or alcohol injection.

Balloon catheters are known in which an expandable, heatable balloon mounted on a catheter shaft can be used as a heat source within a blood vessel during or after angioplasty. These balloon catheters are described in detail in Lennox et al., U.S. Pat. No. 4,955,377, the entire disclosure of which is hereby incorporated herein by reference. Such balloon catheters can also be used in nonvascular applications such as hyperthermia treatment of benign or malignant tumors, or enlargement of the prostate gland. Heat from the balloon destroys undesired cells, which are eventually absorbed into the patient's body.

SUMMARY OF THE INVENTION

It is an important object of the invention to provide a medical system and a method of using the same that enables controlled heating of a very large volume of a solid mass with only a small, atraumatic puncture of the solid mass, by providing an expandable interstitial heating chamber that can be inserted into the solid mass through a puncture site.

In particular, in one aspect of the invention, an elongated, rigid implement having a sharp distal end is insertable into a solid mass within the body of a living being through a puncture site in the solid mass created by the sharp distal end. An elongated sleeve, which engages the elongated, rigid implement, is insertable into the solid mass through the puncture site in the solid mass. Fluid is provided to an expandable chamber located in the vicinity of a distal end of the elongated sleeve through at least one channel located within the elongated sleeve, to inflate the chamber while the chamber is positioned interstitially within the solid mass. A heating device located within the expandable chamber is powered, through at least one elongated conductor located within the elongated sleeve, to heat fluid within the chamber while the chamber is filled with the fluid and is positioned interstitially within the solid mass.

The invention can be used to heat large volumes of tissue in a controlled manner with effectively "scarless" surgery, because the invention uses a heatable chamber that is expandable. In this manner the invention avoids open or laparoscopic surgery. Because the invention does not require a non-expandable electro-surgical probe or a cryo-probe there is no trade-off between probe size and trauma caused by insertion of the probe into the solid mass. Because the invention does not require an interstitial laser fiber there is no concern about a need to limit power to avoid carbon formation at the tip of a fiber. Because the invention does not require injection of alcohol into tissue there is no concern about uncontrolled spread of alcohol beyond the target site.

In addition, the invention enables the volume of fluid introduced into the expandable chamber to be used as a dose parameter, rather than such conventional dose parameters as temperature, power, or time. By varying the geometry of the heating surface defined by the expandable chamber, the volume of heating effect can be varied and controlled.

Yet another advantage of the invention is the ability to necrose tissue through strategic ischemia caused by placing the expandable chamber in the vicinity of feeder vessels that feed the tissue to be necrosed. The combination of vessel compression and heat can result in vessel occlusion. Tissue fed by these vessels will necrose due to ischemia and hypoxia (lack of oxygen). It may be possible to destroy an entire organ or tumor bed by this method.

Because the invention causes local ischemia (reduction in blood flow), color flow doppler imaging may be used as a means of real time guidance for a heating procedure.

In another aspect of the invention the inflation of the chamber while the chamber is positioned interstitially within the solid mass causes compressive ischemia of tissue surrounding the chamber, and the compressive ischemia of the tissue surrounding the chamber reduces a heat sink effect of the tissue during powering of the heating device. Because flow of blood through the tissue is inhibited, heat from the chamber is absorbed into the tissue more effectively than would be the case if the blood could circulate freely through the tissue.

Numerous other features, objects, and advantages of the invention will become apparent from the following detailed description when read in connection with the accompanying drawings.

DETAILED DESCRIPTION

Figure 1:
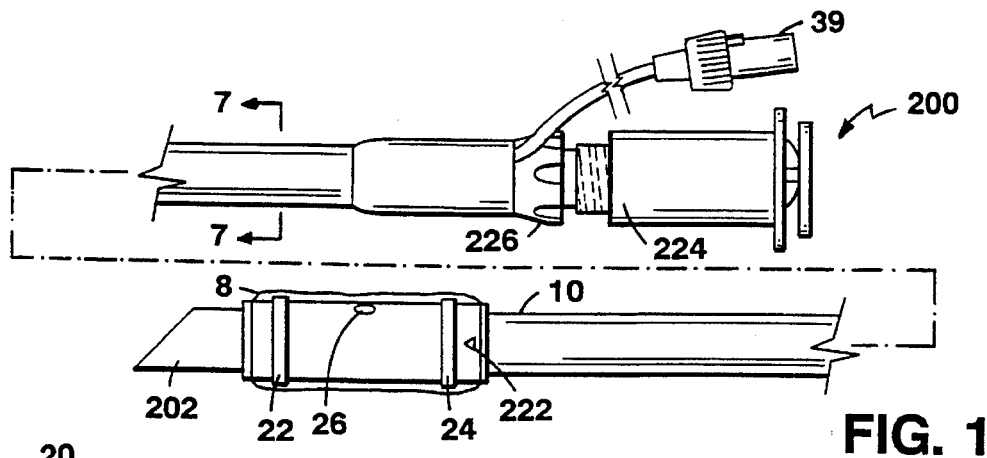
FIG. 1 is a drawing of a medical system having a heatable, expandable balloon mounted on a needle.

Referring to FIGS. 1–7, medical system 200 has a stainless steel, 21-gauge needle 202 having a pointed distal end, a polyimide sheath or sleeve 10 covering all of needle 202 except its tip, and an inflatable elastic balloon 8 in the form of a compliant silicon sleeve having its ends epoxied to sheath 10. Annular electrical contacts 22 and 24 are provided within balloon 8 to cause radio-frequency electrical current to pass through a conductive fluid within the balloon to heat the fluid.

Figure 6:
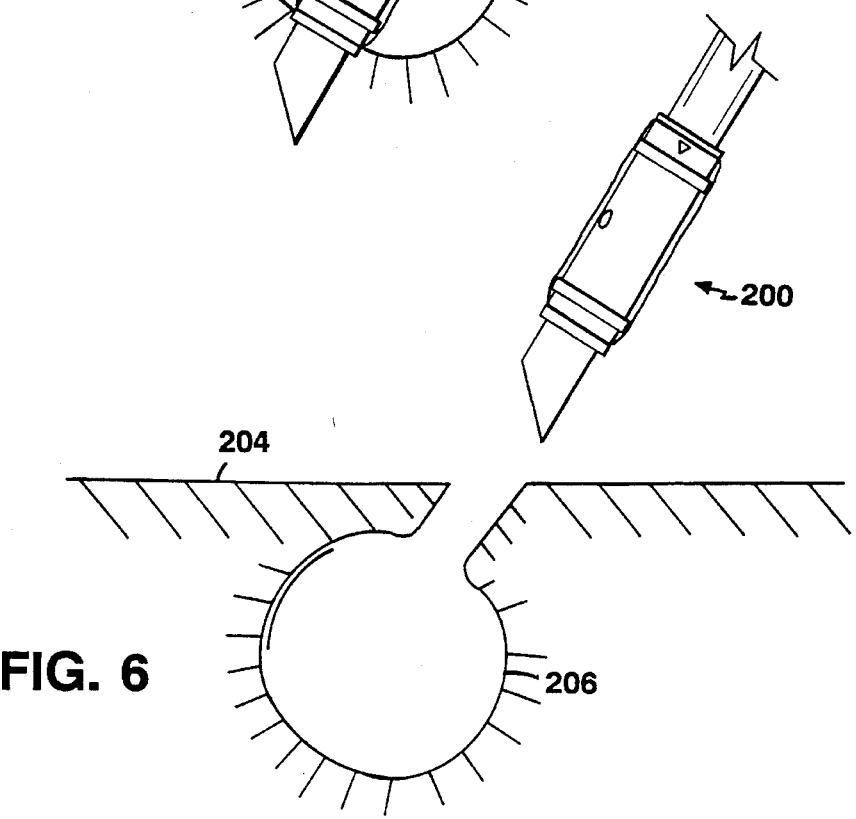
FIG. 6 is a diagrammatic drawing of the medical system of FIG. 1 being removed from the solid organ.
Figure 8:
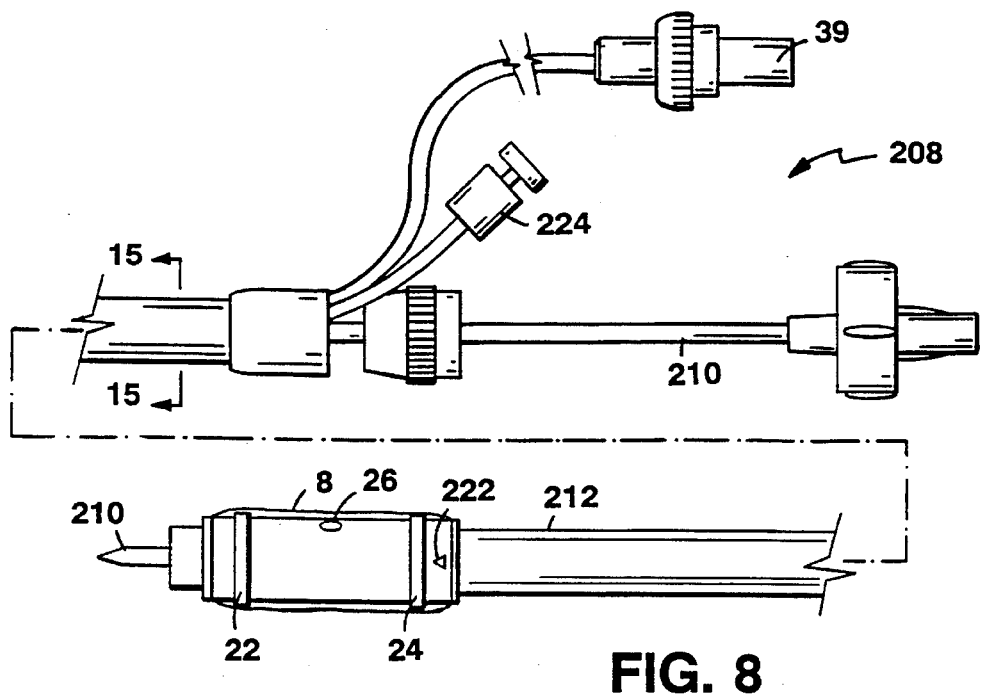
FIG. 8 is a drawing of a medical system having a heatable, expandable balloon mounted on a flexible sheath that slidably surrounds a trocar.
Figure 9:
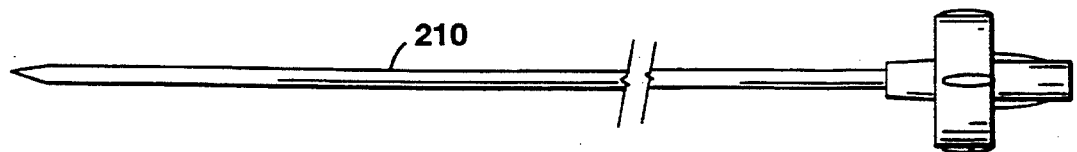
FIG. 9 is a drawing of the trocar of the medical system of FIG. 8.
Figure 10:
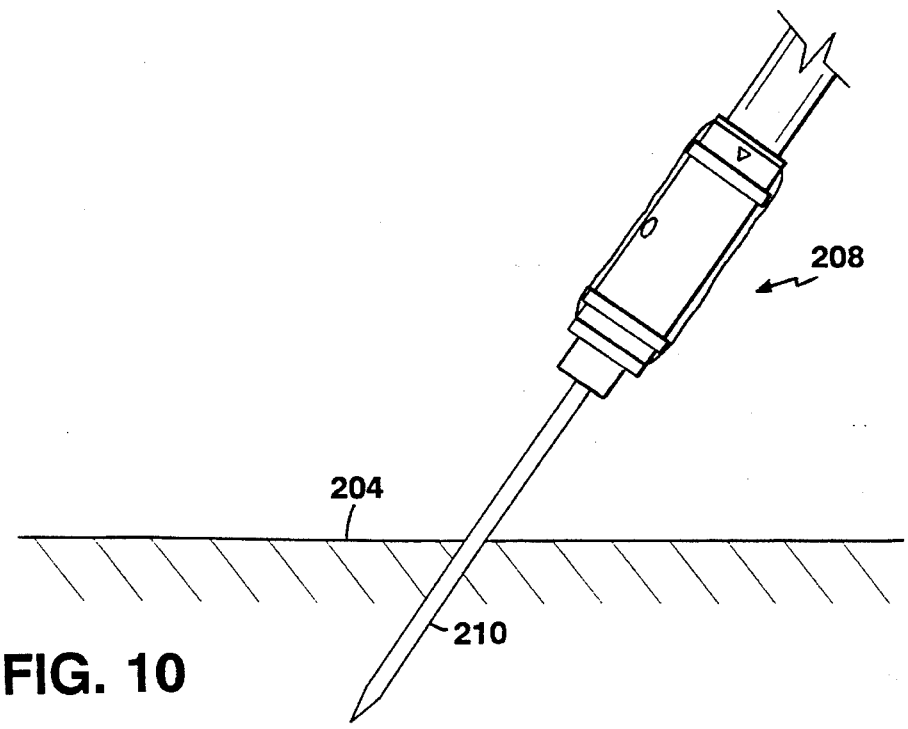
FIG. 10 is a diagrammatic drawing of the medical system of FIG. 8 after the trocar has punctured a solid organ and before the flexible sheath carrying the balloon has entered the solid organ through the puncture site.

During a medical procedure the tip of needle 202 is used to puncture a solid organ 204 (FIGS. 2 and 3) with balloon 8 in a collapsed state. Then, when balloon 8 is positioned interstitially within solid organ 204 in a desired location, balloon 8 is inflated with a desired amount of an electrically conductive fluid 36 (FIG. 4), causing localized compressive ischemia and enlargement of the heating surface (the surface of balloon 8). Electrical current is caused to pass between electrical contacts 22 and 24 within balloon 8 to heat the fluid within the balloon for a desired length of time and at a desired predetermined temperature. The surrounding tissue is heated and necrosed by thermal conductive heat transfer from the balloon surface. The compressive ischemia of tissue reduces the heat sink effect that would otherwise occur due to blood flowing through the tissue. In certain procedures, balloon 8 is then allowed to cool after the heating procedure has been completed, in order to remodel tissue and thereby assist in creation of a cavity 206 within solid organ 204. Then balloon 8 is deflated (FIG. 5), and medical system 200 is removed from solid organ 204 (FIG. 6). If desired, cavity 206 can be filled with ethanol (which slowly leaches into the coagulated tissue), a radioactive seed, an antibiotic, or a chemotherapeutic agent.

The target tissue can be a malignant or benign tumor, a cyst, or hyperplastic tissue causing extrinsic narrowing of a nearby body lumen. The medical system 200 can be used in any solid organ, including the brain, a gland, a lung, a breast, a kidney, the liver, the pancreas, an ovary, or the prostate.

The extent of volumetric heating is a function not only of the temperature differential between the tissue and the heating device, but is also a function of the geometry of the heating source. The larger the diameter, the deeper the heat gradient into the tissue and the larger the necrosis volume. Thus, the amount of fluid used to inflate balloon 8 can be used as a dose parameter.

In certain medical procedures medical system 200 can be used to necrose tissue through strategic ischemia caused by placing balloon 8 in the vicinity of feeder vessels that feed the tissue to be necrosed. The combination of vessel compression and heat can result in vessel occlusion. Tissue fed by these vessels will necrose due to ischemia and hypoxia.

In one embodiment balloon 8 has a wall thickness of about 0.003 or 0.004 inches and is about 1 centimeter long, but the balloon can be longer or shorter depending on the particular medical application. Balloon 8 is fillable with an electrically conductive fluid such as normal saline (0.9 percent NaCl in water), a conductive radiopaque fluid, or a mixture of saline solution and a radiopaque fluid. The fluid passes from syringe 224 through central lumen 220 of needle 202 (diameter about 0.020 inches) and enters balloon 8 through fluid port 222, which is cut through needle 202 and sheath 10. The fluid channel at the proximal end of medical system 200 is terminated by a female luer fitting 226. The volume of balloon 8 can be determined in situ by observing the displacement of the piston of syringe 224.

Annular electrical contacts 22 and 24 inside of balloon 8 have internal diameters matching the portion of the sheath 10 that they surround and are bonded directly to the sheath. In one embodiment the spacing between contacts 22 and 24 is approximately half the length of the balloon, and the spacing from the respective end of the balloon is approximately one fourth the length of the balloon, so that the balloon will heat evenly. The dimensions of the contacts can vary according to the nature of the medical procedure to be performed. In one embodiment the contacts are in the form of annular thin-wall bands having their axial length and diameter about equal. The contacts present a low profile, having a radial thickness of approximately 0.002 inch. The contacts can be made of any conductive material that is compatible with the conductive solution and the conditions of use, and can be made of a radiopaque metal such as platinum or tantalum, so that they may serve as radiopaque markers during placement of the catheter. In one embodiment contacts 22 and 24 are coated with tin, so that they may be soldered by means of tin solder to the wires that connect the contacts to opposing poles of a radio-frequency power supply.

A bead thermistor 26, 0.014 inch in diameter and 0.020 inch long, is mounted directly upon sheath 10 between electrodes 22 and 24. Thermistor 26 fits snugly on top of an opening in the wall of catheter shaft 10 midway between electrodes 22 and 24. An insulating coating of epoxy or urethane seals thermistor 26 on top of the opening on which it rests. A nickel thermistor lead connects thermistor 26 with electrode 22. A wire soldered to the other nickel thermistor lead connects the other thermistor lead with temperature control circuitry.

Figure 7:
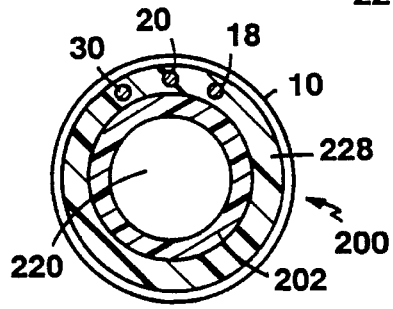
FIG. 7 is a cross-sectional drawing of the medical system of FIG. 1 taken along line 7—7.
Figure 2:
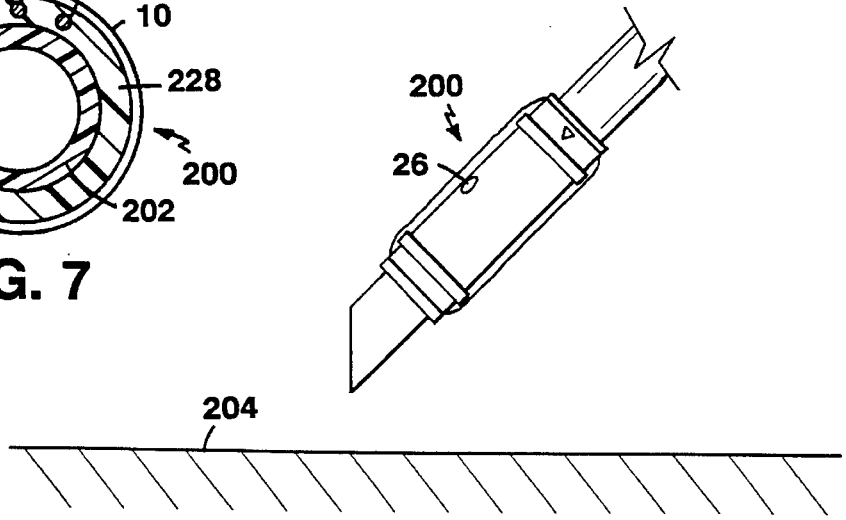
FIG. 2 is a diagrammatic drawing of the medical system of FIG. 1 approaching a solid organ.
Figure 3:
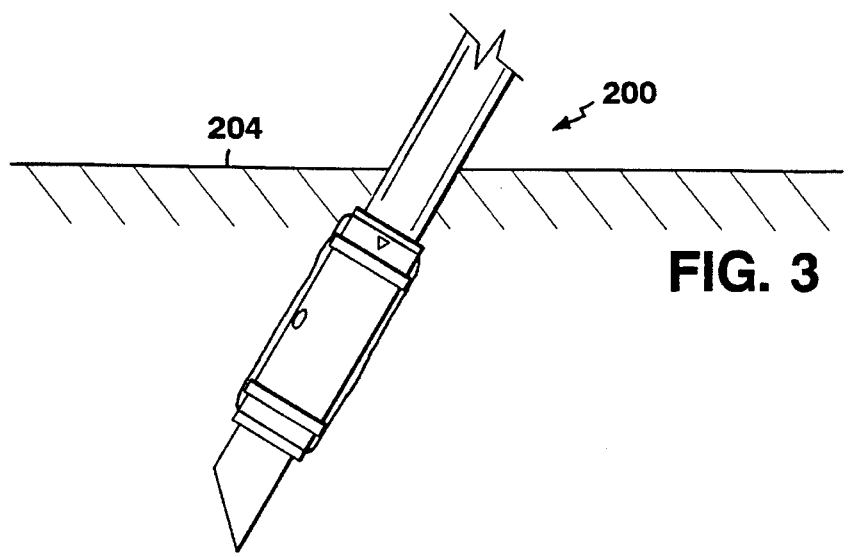
FIG. 3 is a diagrammatic drawing of the medical system of FIG. 1 after the needle has punctured the solid organ.
Figure 4:
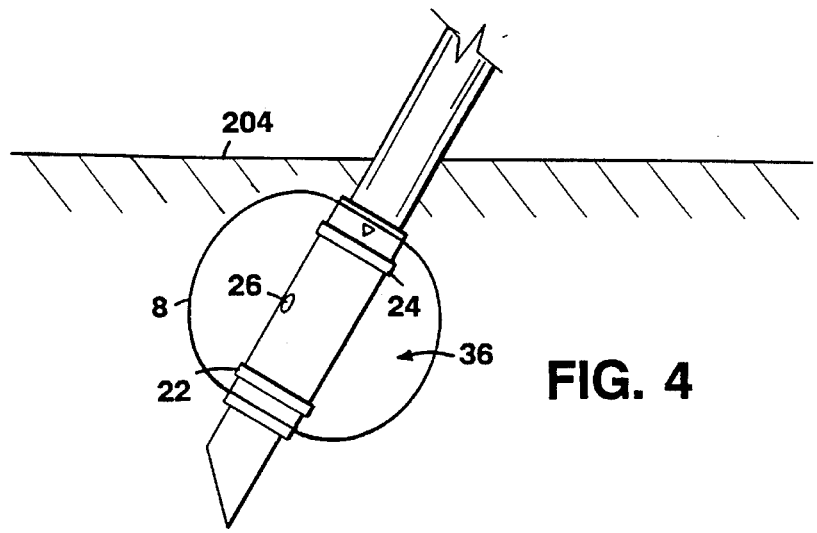
FIG. 4 is a diagrammatic drawing of the medical system of FIG. 1 with the balloon expanded within the solid organ.
Figure 5:
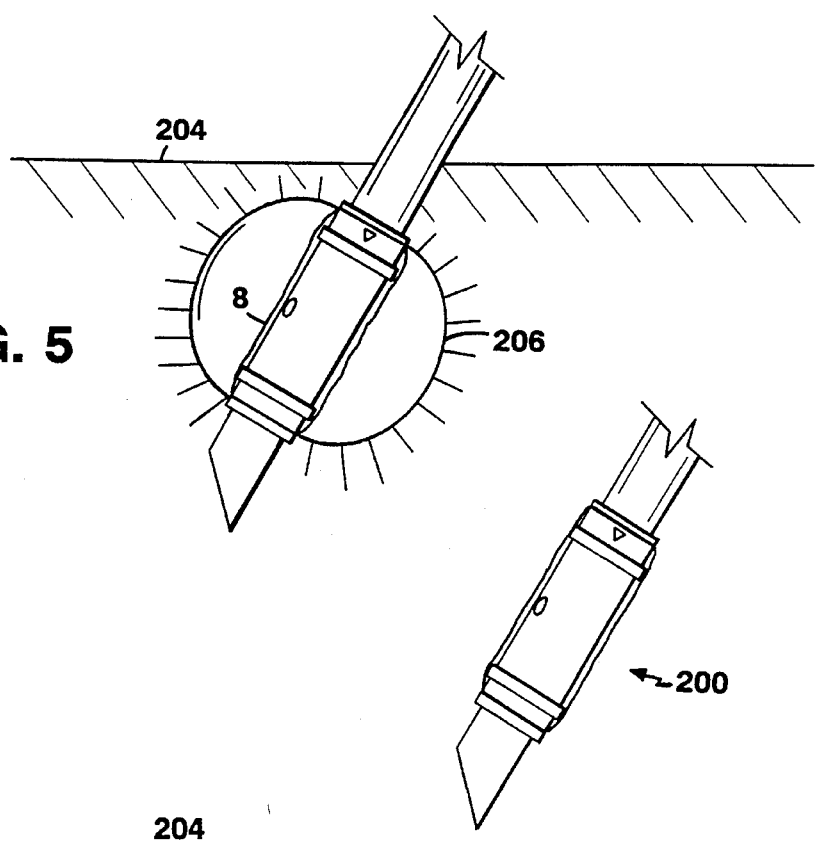
FIG. 5 is a diagrammatic drawing of the medical system of FIG. 1 with the balloon deflated, leaving a cavity within the solid organ.

Referring to FIG. 7, wires 20, 18, and 30 run from the proximal end of medical system 200 all the way to balloon 8 in a space between needle 202 and thin-walled polyimide sheath 10 (outer diameter about 0.035 inches) that is "potted" with a dielectric material 228 that prevents injectate (the balloon inflation fluid) from entering. Wires 20 and 18 connect contacts 22 and 24, respectively, to opposite poles of a current-controlled (constant current) radio-frequency power supply. Wire 30 connects one of the leads of thermistor 26 to temperature control circuitry, and wire 20 (attached to contact 22 which is in turn connected to the other lead of thermistor 26) connects the other lead of thermistor 26 to the temperature control circuitry. Alternatively, two wires can be substituted for wire 20, one wire connecting contact 22 to the radio-frequency power supply and the other wire connecting the thermistor lead directly to the temperature control circuitry.

The RF power supply used to apply a radio-frequency electrical potential between contacts 22 and 24 operates at 650 kilohertz, but can alternatively operate at any frequency within the range of about 100 kilohertz to 1 megahertz. It is important to use radio frequency power rather than direct or low frequency current, or microwave power, because the risk of a physiological response or electrocution response is reduced at RF frequencies above 100 kHz kilohertz as compared with d.c. or low frequencies, and because microwave power would lead to radiative losses in wires 18 and 20, that can result, e.g. in unwanted heating of sheath 10. The fluid 36, while selected to have resistive losses, has an electrical impedance low enough that it will conduct the current supplied by the RF power supply at voltages of about 100 volts or lower, so that there will be no arcing across insulated wires 18 and 20. For example, if the current I is set at 1 amp, and the impedance R between the electrodes and through the fluid is 100 ohms, the voltage V will be 100 volts according to V=IR, and the power P dissipated into the fluid will be 100 watts, according to $P=I^2R$. In general, where two electrodes are employed, the impedance between the electrodes will be less than 1000 ohms, e.g., in the range of 50 to 500 ohms, or about 100 ohms.

In all events the shape of the balloon and the construction and spacing of the electrical contacts are preselected so that the electrical current is substantially confined to the interior of the balloon.

Medical system 200 plugs into the RF power supply and temperature control circuitry by means of a plug 39, which is keyed with respect to the particular size of medical system it is associated with, to cause the power supply to operate at a maximum current of 1/10, 1/4, 1/2 or 1 amp. Plug 39 has seven pins, three of which are needed to operate the catheter. During manufacture, a jumper connection is made within plug 39 between a selected two of the remaining four pins. The jumper connection indicates how much current, at maximum, the RF power supply should produce, depending upon which pins the jumper connection connects. Thus, the user need only select the appropriate medical system, and need not be concerned about selecting the appropriate maximum current.

If balloon 8 contains conductive radiopaque fluid, the location of balloon 8 can be monitored by means of radiography. Alternate guidance techniques include ultrasonography, MRI, and palpation. In addition, because the invention causes local ischemia, color flow doppler imaging may be used as a means of real time guidance for a heating procedure.

Referring to FIGS. 8–15, another medical system 208 according to the invention has a stainless steel trocar 210 and a flexible nylon sheath 212 that slidably engages trocar 210 through a longitudinally extending lumen 214 within sheath 212. Inflatable, silicon balloon 8 has its ends bonded to sheath 212.

Figure 11:
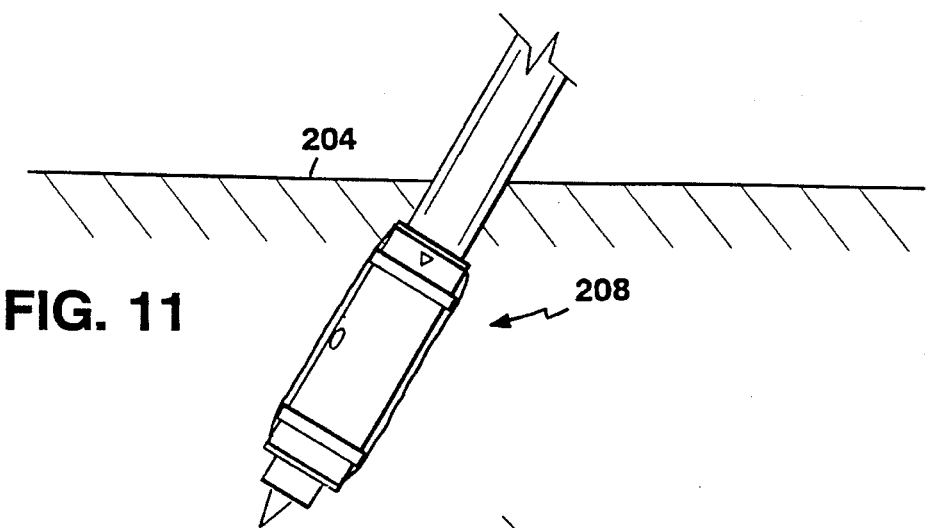
FIG. 11 is a diagrammatic drawing of the medical system of FIG. 8 after the flexible sheath carrying the balloon has entered the solid organ.
Figure 12:
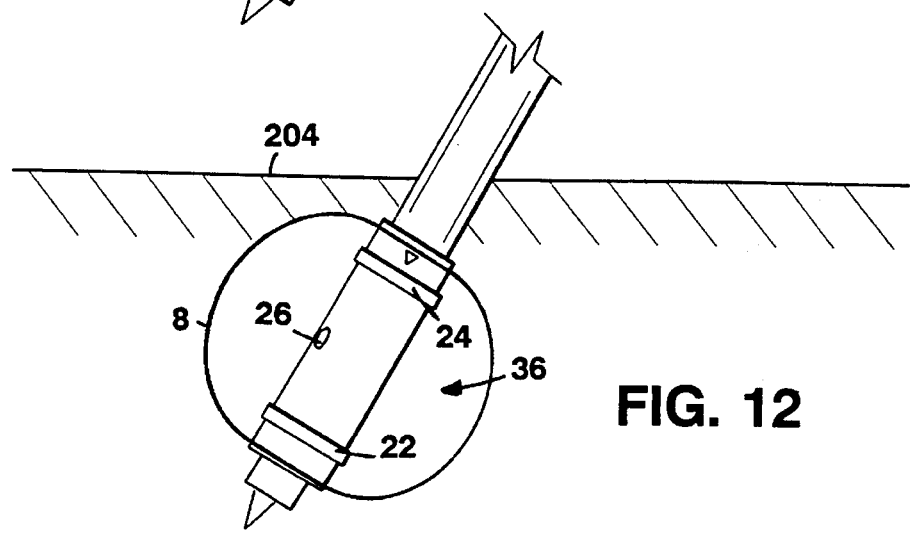
FIG. 12 is a diagrammatic drawing of the medical system of FIG. 8 with the balloon expanded within the solid organ.
Figure 13:
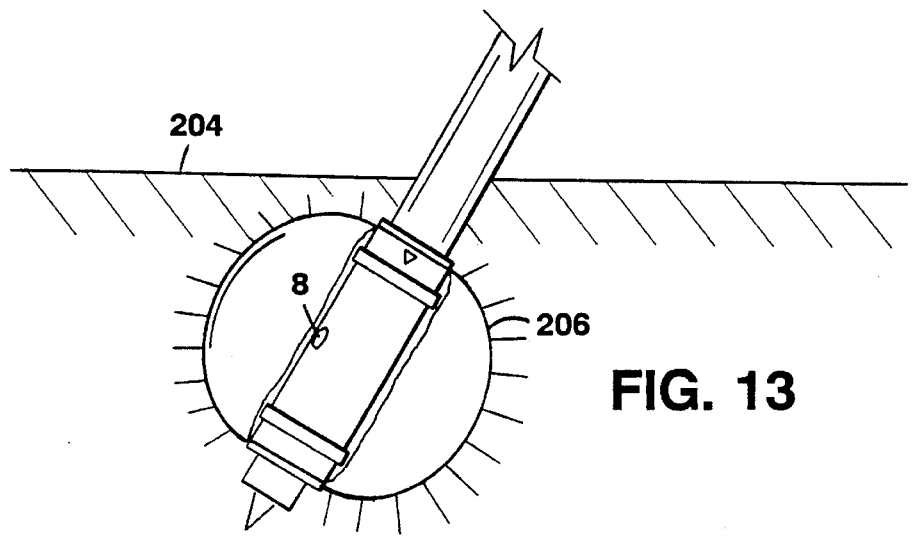
FIG. 13 is a diagrammatic drawing of the medical system of FIG. 8 with the balloon deflated, leaving a cavity within the solid organ.
Figure 14:
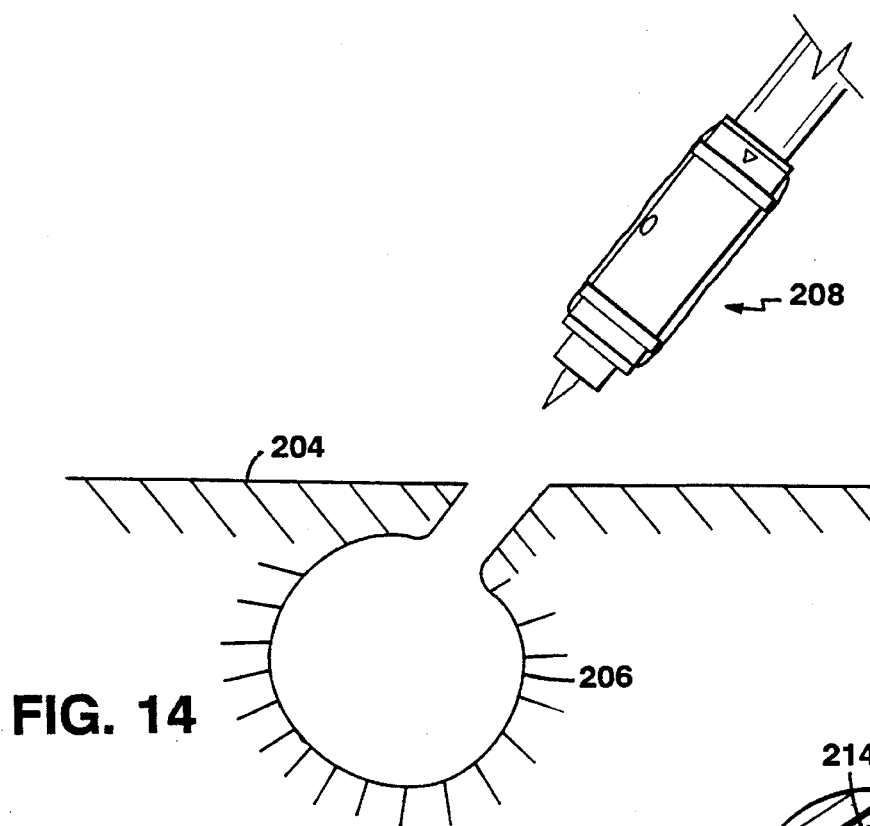
FIG. 14 is a diagrammatic drawing of the medical system of FIG. 8 with the trocar and the flexible sheath carrying the balloon being removed from the solid organ.

During a medical procedure the tip of trocar 210 is used to puncture a solid organ 204 (FIG. 10) and then sheath 212 is guided over trocar 210 through the puncture site to the target tissue in solid organ 204 until balloon 8 is positioned interstitially within solid organ 204 in a desired location (FIG. 11). Then balloon 8 is inflated (FIG. 12) and electrical current is caused to pass between electrical contacts 22 and 24 to heat the fluid within the balloon. After the heating procedure has been completed balloon 8 is deflated (FIG. 13) and, in certain procedures, is allowed to cool, leaving a cavity 206 within solid organ 204. Medical system 200 is then removed from solid organ 204 (FIG. 14).

The trocar embodiment of FIGS. 8–15 is especially useful in interstitial heating of soft and pliable organs such as the liver or pancreas. In particular, the position of such organs relative to the patient's skin can be susceptible to change. In use of the trocar embodiment of FIGS. 8–15 rigid trocar 210 can be removed from the soft organ after flexible sheath 212 has been inserted into the organ but before inflation of balloon 8.

Alternatively, trocar 210 may remain in place within solid organ 204 after flexible sheath 212 has been removed, and another medical instrument may be slid over trocar 210 to inject ethanol, a radioactive seed, an antibiotic, a chemotherapeutic agent, etc. into the solid organ.

Figure 15:
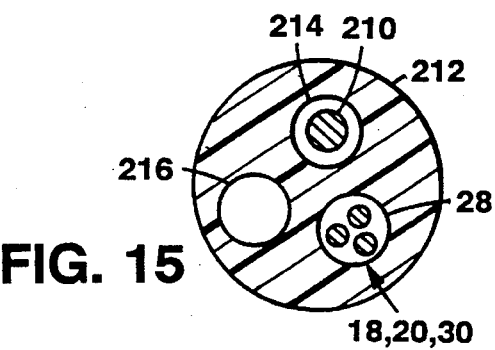
FIG. 15 is a cross-sectional drawing of the medical system of FIG. 8 taken along line 15—15.

Referring to FIG. 15, flexible nylon sheath 212 (outer diameter about 0.048 inches or smaller) has three lumens 214, 216, and 218. Lumen 214 (diameter about 0.020 inches) extends from the proximal end of sheath 212 to the distal end, and slidably engages trocar 210 (outer diameter about 0.018 inches). Lumen 216 extends from syringe 224 at the proximal end of the catheter shaft 10 to fluid port 222 in the inside of balloon 8, and provides a conduit for injectate fluid 36 as balloon 8 is inflated and deflated. Lumen 218 extends from the proximal end of catheter shaft 10 to the inside of balloon 8, and provides a conduit for wires 18, 20, which are connected to electrodes 24 and 22 respectively, and wire 30, which is connected to one of the leads of thermistor 26 (the other lead of thermistor 26 being connected to electrode 22 as described above in connection with the embodiment of FIGS. 1–7). Lumen 218 is "potted" with a high dielectric strength material that prevents injectate from entering the lumen.

Figure 16:
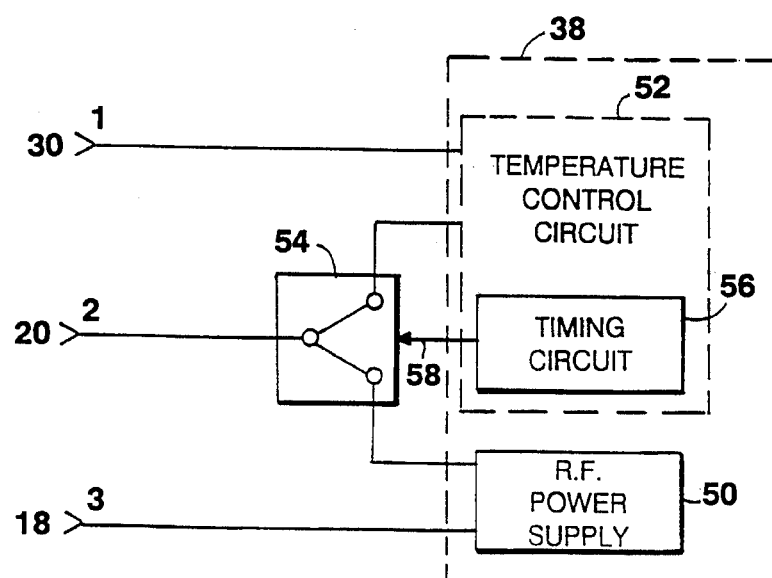
FIG. 16 is a block diagram of the radio-frequency power supply and temperature control circuitry for use in conjunction with the medical systems of FIG. 1 and FIG. 8.

Referring to FIG. 16, RF power supply and temperature control circuitry 38, for use with the embodiment of FIGS. 1–7 and the embodiment of FIGS. 8–15, consists of RF power supply 50, temperature control circuit 52, and solid state switch 54. Wire 18 connects electrode 24 with RF power supply 50, and wire 30 connects thermistor 26 with temperature control circuit 52. Timing circuit 56 of temperature control circuit 52 toggles hold/NOT sample line 58 so that solid state switch 54 toggles back and forth, whereby wire 20 functions alternately as a lead connecting RF power supply 50 with electrode 22 and as a lead connecting temperature control circuit 52 with thermistor 26 (recall that electrode 22 is connected to one of the leads of thermistor 26). The temperature sensing period is 1 percent of the 60 hertz cycle. When solid state switch 54 connects wire 20 with temperature control circuit 52, temperature control circuit 52 determines how much power, at maximum, RF power supply 50 should supply when solid state switch 54 next connects wire 20 with RF power supply 50. By thus multiplexing between temperature sensing and application of current to the electrodes, the temperature control circuitry eliminates the possibility that thermistor 26 will pick up RF noise from electrodes 22 and 24.

Figure 17:
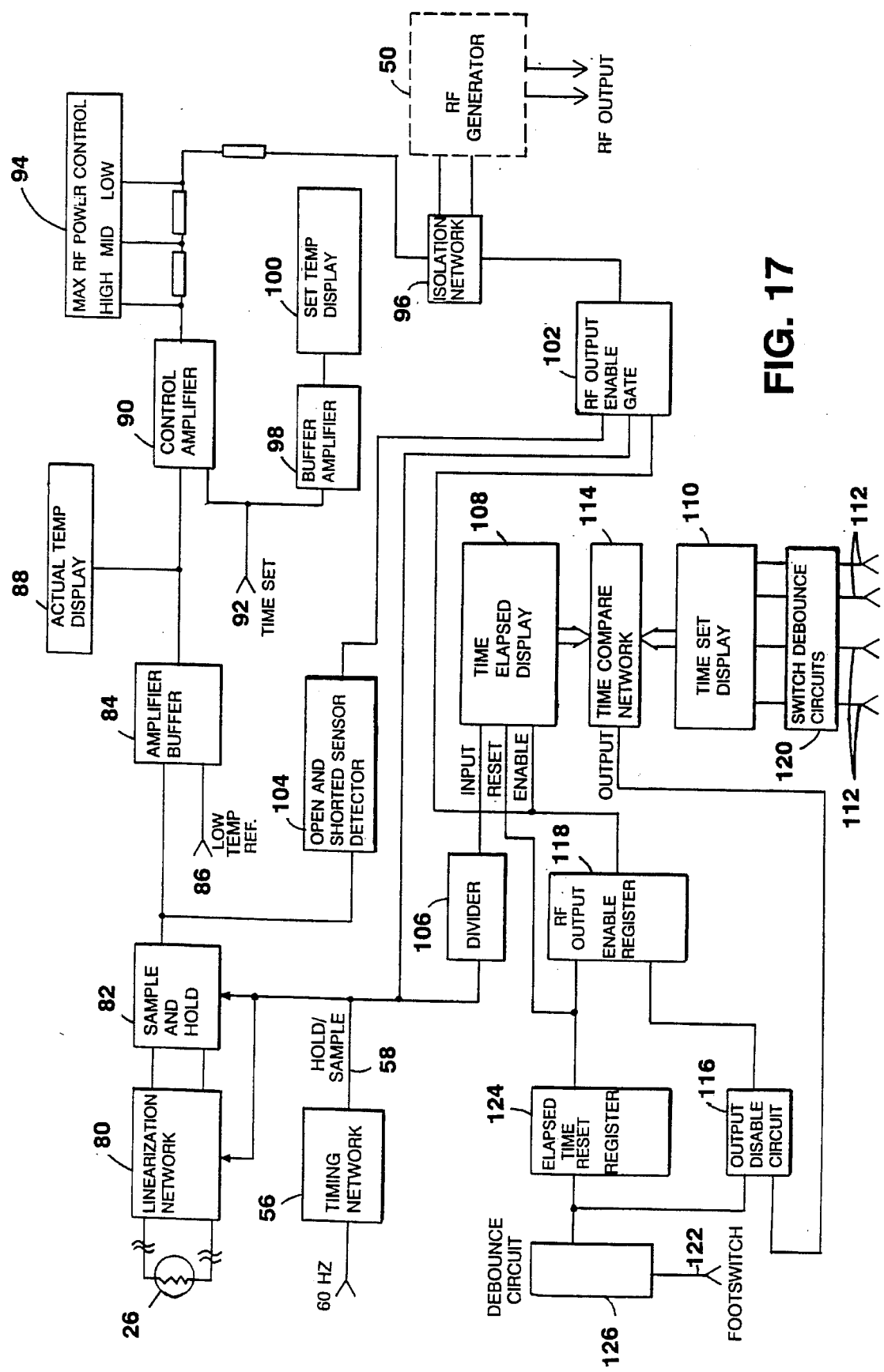
FIG. 17 is a detailed block diagram of temperature control circuitry for use in conjunction with the medical systems of FIG. 1 and FIG. 8.

Referring to FIG. 17, in temperature control circuit 52, linearization network 80 linearizes the input signal from temperature sensor 26 and delivers the linearized signal to sample and hold register 82. The signal is delivered to amplifier buffer 84 having low-temperature reference 86. Actual temperature display circuit 88 displays the output of amplifier buffer 84. Control amplifier 90 compares the output of amplifier buffer 84 with a temperature set voltage 92 that is set by the user. The maximum RF power control circuit 94 receives the output of control amplifier 90 and determines the level of RF power, at maximum, that the RF power supply 50 should produce. The signal from the maximum RF power control circuit 94 is received by isolation network 96, which interfaces with RF power supply 50. The temperature set voltage 92 is received by buffer amplifier 98 and displayed by set temperature display 100.

Timing circuit 56 toggles hold/NOT sample line 58 at 60 hertz, so that hold/NOT sample line 58 is low during 1 percent of the cycle and high during the other 99 percent of the cycle. Hold/NOT sample line 58 is low when signals from temperature sensor 26 are being sampled and high when signals from temperature sensor 26 are not being sampled. Hold/NOT sample line 58 is received by RF output enable gate 102. The output of sample and hold register 82 is processed by open and short sensor detector 104 to determine whether a sensor malfunction, such as a shorted or open sensor, has occurred. The output of open and shorted sensor detector 104 is received by RF output enable gate 102. RF output enable gate 102 delivers a signal to isolation network 96, which turns off RF power supply 50 when there has been a sensor malfunction or when signals from temperature sensor 26 are being sampled.

Divider 106 receives hold/NOT sample line 58 and delivers its output to time elapsed display 108. Time set display 110 displays the time indicated by time set switches 112, which are set by the user. Time compare network 114 compares the elapsed time with the time set by the user, and delivers an output signal to output disable circuit 116. The output of output disable circuit 116, which is active only when the elapsed time is less than the time set by the user, is delivered to RF output enable register 118. RF output enable register 118 in turn delivers the signal to the enable input to time elapsed display 108, and also to RF output enable gate 102, so that RF power supply 50 may be turned off when the time set by the user has elapsed. Switch debounce circuits 120 are provided for time set switches 112.

The user must depress footswitch 122 in order for RF power supply 50 to operate. While footswitch 122 is activated, and while the elapsed time is less than the time set by the user, output disable circuit 116 delivers a signal to RF output enable register 118, which in turn delivers the signal to the enable input of time elapsed display 108, and also to RF output enable gate 102 so that RF power supply 50 may be turned on. Deactivation of footswitch 122 causes a signal to pass through elapsed time reset register 124, in order to reset time elapsed display 108 and in order to reset RF output enable register 118. The resetting of RF output enable register 118 causes RF output enable gate 102 to turn off RF power supply 50. Debounce circuit 126 is provided for footswitch 122.

In use of the temperature control circuitry, the user first preselects the desired therapeutic temperature (temperature set voltage 92), and sets the length of time for which balloon 8 is to be heated (time set switches 112, FIG. 6). When balloon 8 inflated to at least a low level of pressure, the user depresses footswitch 122 to initiate the bi-polar heating between the electrodes. Heat is dissipated into the fluid according to the formula $P=I^2R$ where P is the power that is dissipated into the fluid, I is the current that is passed through the electrodes, and R is the resistance of the fluid. The heat from the fluid is conducted across the balloon wall into the surrounding tissue. The fluid will heat to the temperature set by the user. Heating will continue until the time set by the user has elapsed, or until the user deactivates footswitch 122.

There has been described novel and improved apparatus and techniques for interstitial heating of tissue. It is evident that those skilled in the art may now make numerous uses and modifications of and departures from the specific embodiment described herein without departing from the inventive concept. For example, the fluid within the balloon can be heated by methods other than the one specifically described above.

What is claimed is:

1. A medical system for interstitial heating of a solid mass within a body of a living being, comprising:

an elongated, rigid implement having a sharp distal end and constructed for insertion into said solid mass through a puncture site in said solid mass created by said sharp distal end, an elongated sleeve constructed to engage said elongated, rigid implement and constructed to enter said solid mass through said puncture site in said solid mass and to extend into said solid mass, an expandable chamber located in the vicinity of a distal end of said elongated sleeve, at least one channel located within said elongated sleeve to provide a fluid to said expandable chamber for inflation of said chamber while said chamber is positioned interstitially within said solid mass, a heating device located within said expandable chamber for heating said fluid within said chamber while said chamber is filled with said fluid, and at least one elongated conductor located within said elongated sleeve and connected to said heating device to power said heating device while said chamber is positioned interstitially within said solid mass and is filled with said fluid.

2. A medical system in accordance with claim 1 wherein said elongated, rigid implement comprises a needle.

3. A medical system in accordance with claim 1 wherein said elongated rigid implement comprises a trocar.

4. A medical system in accordance with claim 1 wherein said elongated rigid implement and said elongated sleeve are separate and distinct elements.

5. A medical system in accordance with claim 1 wherein said elongated sleeve is mounted directly on said elongated rigid implement.

6. A medical system in accordance with claim 1 wherein said elongated sleeve is constructed to slidably engage said elongated rigid implement.

7. A medical system in accordance with claim 6 wherein said elongated sleeve has a channel extending longitudinally through said elongated sleeve, said channel having dimensions suitable for slidably engaging said elongated, rigid implement.

8. A medical system in accordance with claim 1 wherein said expandable chamber comprises a balloon.

9. A medical system in accordance with claim 1 wherein said expandable chamber is mounted directly on said elongated sleeve.

10. A medical system in accordance with claim 1 wherein said heating device heats said fluid within said expandable chamber by causing electrical current to pass through a resistive pathway within said chamber.

11. A medical system in accordance with claim 10 wherein said heating device comprises a plurality of electrodes and wherein there are a plurality of elongated conductors extending through said elongated sleeve, said conductors being connected to respective ones of said plurality of electrodes to provide a radio-frequency electrical potential between said electrodes while said chamber is filled with said fluid and thereby to cause said fluid to be heated by resistive losses of electrical current passing through said fluid, said fluid being electrically conductive.

12. A method of interstitially heating a solid mass within a body of a living being, comprising the steps of:

inserting an elongated, rigid implement having a sharp distal end into said mass through a puncture site in said solid mass created by said sharp distal end, inserting an elongated sleeve, which engages said elongated, rigid implement, into said solid mass through said puncture site in said solid mass, providing a fluid to an expandable chamber located in the vicinity of a distal end of said elongated sleeve through at least one channel located within said elongated sleeve, to inflate said chamber while said chamber is positioned interstitially within said solid mass, and powering, through at least one elongated conductor located within said elongated sleeve, a heating device located within said expandable chamber and connected to said at least one elongated conductor, to heat said fluid within said chamber while said chamber is filled with said fluid and is positioned interstitially within said solid mass.

13. A method in accordance with claim further comprising the step of causing tissue surrounding said chamber to be displaced by said step of providing fluid to said expandable chamber to inflate said chamber while said chamber is positioned within said solid mass.

14. A method in accordance with claim 13, further comprising the step of causing compressive ischemia of said tissue by displacement of said tissue.

15. A method in accordance with claim 13 wherein said step of inserting said elongated sleeve into said solid mass comprises positioning said chamber in the vicinity of feeder vessels that feed tissue to be necrosed, and wherein said method comprises the step of necrosing said tissue by occluding said feeder vessels through said step of providing fluid to said expandable chamber to inflate said chamber and said step of powering said heating device.

16. A method in accordance with claim 12, further comprising the step of remodeling tissue within said solid mass by allowing said chamber to cool while said chamber is positioned interstitially within said solid mass.

17. A method in accordance with claim 12 further comprising the step of monitoring interstitial heating of said solid mass by non-invasive ultrasound.

18. A method in accordance with claim 12, further comprising the step of monitoring the amount of said fluid provided to said expandable chamber, as a dose parameter of interstitial heating of said solid mass.

19. A method in accordance with claim 12 further comprising the step of monitoring ischemia within said solid mass by color flow doppler imaging.

20. A method of interstitially heating a solid mass within a body of a living being, comprising the steps of:

inserting an elongated, rigid implement having a sharp distal end into said mass through a puncture site in said solid mass created by said sharp distal end, inserting an elongated sleeve, which engages said elongated, rigid implement, into said solid mass through said puncture site in said solid mass, providing a fluid to an expandable chamber located in the vicinity of a distal end of said elongated sleeve through at least one channel located within said elongated sleeve, to inflate said chamber while said chamber is positioned interstitially within said solid mass, powering, through at least one elongated conductor located within said elongated sleeve, a heating device located within said expandable chamber and connected to said at least one elongated conductor, to heat said fluid within said chamber while said chamber is filled with said fluid and is positioned interstitially within said solid mass, and reducing a heat sink effect of said tissue surrounding said chamber during powering of said heating device by causing compressive ischemia of said tissue through said step of providing said fluid to said chamber.

* * * * *